United States Patent [19]

Schaffer et al.

[11] Patent Number: 4,684,367

[45] Date of Patent: Aug. 4, 1987

[54] AMBULATORY INTRAVENOUS DELIVERY SYSTEM

[75] Inventors: Irving Schaffer, Fairfield, Conn.; Claude L. Emmerich, Scarsdale, N.Y.

[73] Assignee: Meditec Research Associates, Westport, Conn.

[21] Appl. No.: 722,934

[22] Filed: Apr. 12, 1985

[51] Int. Cl.⁴ .............................................. A61M 5/00
[52] U.S. Cl. ..................................... 604/140; 604/67; 604/262; 604/141; 128/DIG. 12; 128/DIG. 13; 73/204
[58] Field of Search ..................... 604/65, 66, 67, 113, 604/140, 262, 141; 128/736, DIG. 12, DIG. 6, DIG. 13; 73/204

[56] References Cited

U.S. PATENT DOCUMENTS

| 4,043,332 | 8/1977 | Metcalf | 128/DIG. 13 |
| 4,083,244 | 4/1978 | Agar et al. | 73/204 |
| 4,270,533 | 6/1981 | Andreas | 128/DIG. 12 |
| 4,430,078 | 2/1984 | Sprague | 604/141 |
| 4,432,468 | 2/1984 | Siff et al. | 604/65 |
| 4,458,709 | 7/1984 | Springer | 73/204 |
| 4,576,182 | 3/1986 | Normann | 128/736 |

FOREIGN PATENT DOCUMENTS 2747593  4/1979  Fed. Rep. of Germany ...... 604/141

Primary Examiner—Stephen C. Pellegrino
Assistant Examiner—John D. Ferros
Attorney, Agent, or Firm—Pennie & Edmonds

[57] ABSTRACT

An apparatus for ambulatory intravenous delivery of substances to a recipient comprising a container and delivery means for pressurized delivery of the substance. The container communicates with a source of pressurized gas to provide the pressurizing force and is uniquely attachable to the recipient so as to provide portability to the system. The flow rate is controlled by feedback electronics connected to a flow rate meter and a throttle valve. The flow rate meter has a heating resistor in the flow path of the substance and a thermistor to detect a temperature rise in the substance downstream from the resistor. A constriction in the flow tube is disposed between the resistor and thermistor to cause a flat wavefront of temperature increase. The throttle valve is a pin disposed partially within a tube to form an annular gap. The flow rate is adjusted by changing the distance the pin extends into the tube and thereby change the length of the annular gap.

27 Claims, 11 Drawing Figures

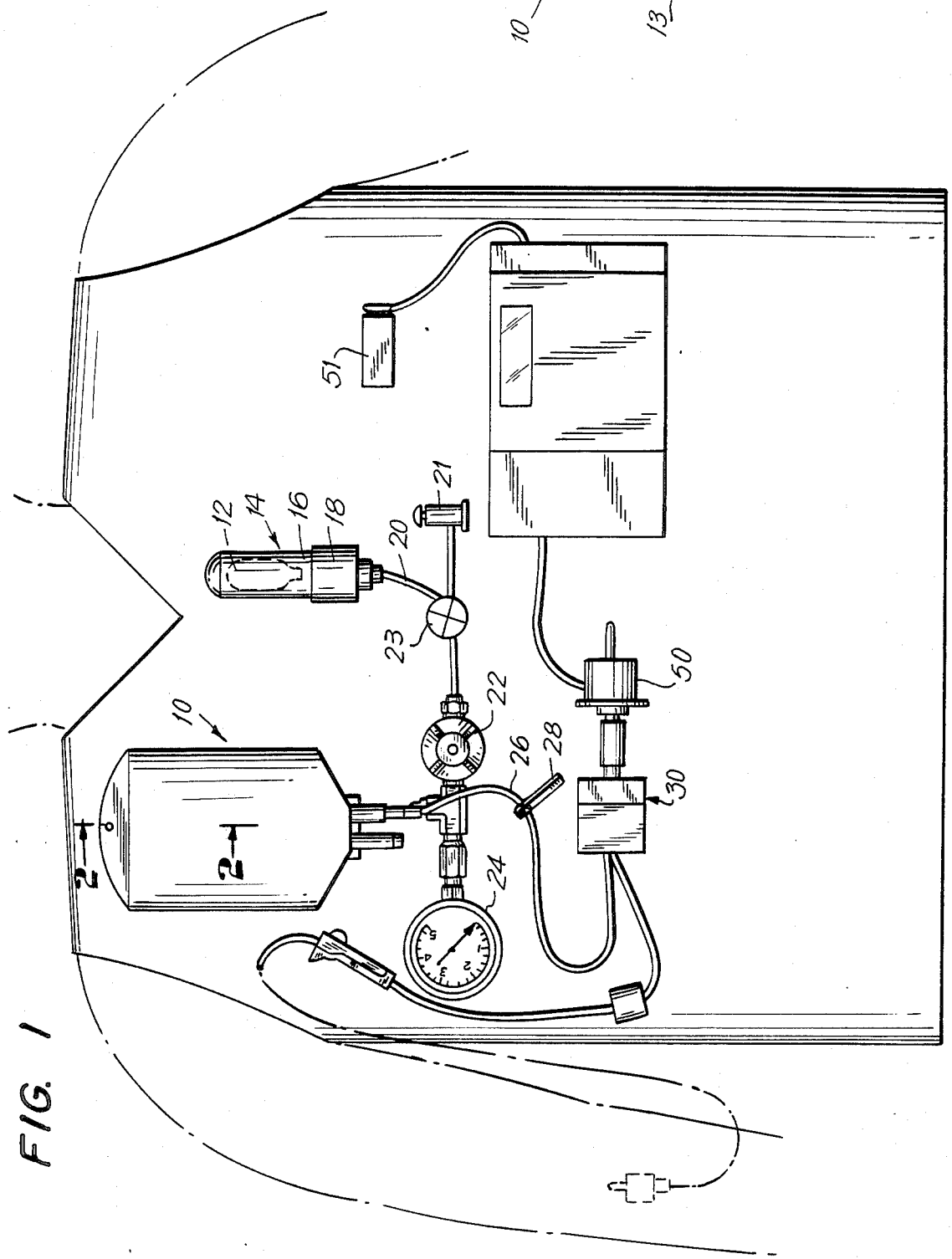
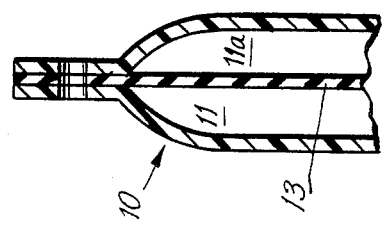

AMBULATORY INTRAVENOUS DELIVERY SYSTEM

BACKGROUND OF THE INVENTION

1. Field of the Invention

The invention relates to intravenous delivery systems and in particular to ambulatory intravenous delivery systems which provide a metered flow while allowing the patient to move about.

2. Background Art

In current medical technology, there exists a variety of devices that deliver intravenous fluids and chemotherapy to patients. Some of these devices offer some degree of portability, however, the majority of these devices confine a patient to bed. Portable or so called "ambulatory" devices usually work on an infusion pump delivery principle. That is, a system which pumps the substance into the patient to overcome the resistance of patient pressure. The system is operated without actual flow measurement being fed back into the system therefore the control available in these devices is greatly limited. These devices in most cases place a minimum of importance on patient comfort and convenience.

Normally, the various infusion pump systems that generate their own pressure to overcome the resistance of patient pressure do not contain means for controlling fluid flow at the various pressures required. The common stationary gravity feed units provide limited control possibilities by altering the height of the container above the patient, but this requires an apparatus upon which to hang the container. Such an apparatus greatly limits portability of the unit.

The known volumetric peristaltic or piston-cylinder pumps have large power requirements and therefore require frequent battery replacement. Higher viscosity fluids such as hyperalimintation solutions are limited to use with these devices and races lower than 100 ml/hr.

In "unmonitored" units, that is units where the flow rate is not checked against the requested flow rate, poorly regulated or uneven flow may be disastrous. In the unmonitored type of unit, the flow rate is easily affected by such factors as tubing position, patient arm height or arm orientation.

Thus, while various systems are known for providing intravenous delivery of fluids to a patient, there is no single system that allows the patient to be ambulatory in and out of a hospital and where the device can deliver larger quantities of fluid such as 500 ml/hr at various pressures, maintaining precisely controlled rates, or even as low as 10 ml/hr, with a minimum of battery power, control feedback and maximum possible comfort for the patient.

SUMMARY OF THE INVENTION

The invention relates to an apparatus for intravenous delivery of substances while permitting the recipient to be ambulatory comprising: means for containing and delivering a substance to be delivered to the recipient, said containing means capable of being supported and carried by the recipient; means communicating with said container; means for providing pressure to the substance to be delivered; means to control the flow rate of the substance to the recipient; means to determine the flow rate of the substance and to produce a signal indicating such flow rate and means to adjust the flow control means in response to the signal indicating the flow rate so as to maintain a predetermined flow rate of the substance.

Advantageously the containing means may comprise a container having at least two compartments separated by suitable means to transfer pressure therebetween, such as a membrane or other flexible divider. The first compartment is for containing the substance to be delivered and communicates with the delivery means. The second compartment communicates with a source of pressurized gas such that the pressure of the second compartment acts on the first compartment to force the substance out of the first compartment. The pressure in the second compartment may be regulated by a regulator means disposed between the source of compressed gas and the second compartment and the source of pressurized gas may be a cartridge containing pressurized gas such as a $CO_2$ cartridge.

The flow control means may comprise an exit tube, an inlet tube having a wall of predetermined diameter, a reservoir portion which communicates with the exit tube and the inlet tube, a control pin of predetermined diameter which is less than the diameter of the inlet tube and is movably disposed within the inlet tube such that flow of the fluid through said inlet must flow through the annular gap between the pin and the wall of the inlet tube, and means to adjust the distance which said pin extends into said inlet tube.

The diameter of the inlet tube may increase in the direction of flow to increase the size of the annular gap and the means to control the flow control means may be a stepper motor controlled by electronic circuitry.

The means to determine the flow rate may comprise metering means including a first tubular section, a second tubular section of lesser cross-sectional area than the first section, a third section of cross-sectional area larger than the second section. The second section is disposed between the first and third sections. Heating means are disposed within the first section to supply heat to a portion of the substance as it flows therethrough. Detecting means are disposed within the third section to detect temperature changes in the substance as it flows therethrough. The structure is such that a pulse of heat may be intermittently added to the substance by the heating means and detected down stream by the detecting means to determine the flow rate of the substance. The heating means may be a chip electrical resistor. The detecting means may be a thermistor whose resistance varies with temperature.

The means to determine flow rate of the substance and signal producing means may further comprise electronic circuitry. The electronic means may provide a signal to the flow control means to vary the flow rate of the substance in response to the flow rate determination and in comparison to a predetermined flow rate command.

The invention includes a new apparatus for regulating the flow rate of a fluid comprising a housing with an inlet opening to allow fluid to enter said housing and an outlet opening to allow fluid to exit said housing, the inlet opening is circular and communicates with an inlet tube of cylindrical internal wall shape, a cylindrical pin of lesser diameter than the internal diameter of the inlet tube has a first portion movably disposed within the inlet tube forming an annular gap between the internal wall of the inlet tube and the cylindrical surface of the pin. The pin has a second portion which extends into the housing and means are provided to move the pin so as to adjust the distance which the pin extends into the inlet tube to adjust the length of the annular gap through which the fluid flows.

The means to move the pin in the apparatus for regulating the flow rate of a fluid may be a flexible diaphragm disposed within the housing attached to an end on the second portion of the pin, on the opposite side of the diaphragm is a stepper motor with a shaft. The stepper motor is capable of moving its shaft incremental amounts in the axial direction. One end of the stepper motor shaft is fixed to the diaphragm on the reverse surface of the diaphragm such that when the stepper motor operates to axially move the shaft, the shaft flexes the diaphragm to move the pin.

Also novel is the above-described metering means, which has three sections. The second section is disposed between the first and third sections and causes the substance flow path to be through a step constriction and a step enlargement of cross-sectional area. Heating means are disposed within the first section to supply predetermined and pre-timed heat pulses to the substance. Temperature detecting means is disposed within the third section to detect temperature changes in the substance as it flows through the third section. The fluid flows first through the first section then through the second section then through the third section. Means to measure the first lapse between a heating pulse and the detection thereof by detecting means is provided to determine flow rate. Optionally the heating means is an electrical chip resistor. The detecting means may be a thermistor disposed within the third section.

As can be seen, the present invention is a precisely controlled ambulatory intravenous (i.e. I.V.) delivery system that can be worn in a number of ways, such as vestmount, waistmount or attached to the forearm. The unit is completely self-contained in any of the configurations and is developed for maximum patient comfort. The device intravenously delivers fluids at any pressure. The system pressure remains constant even as the I.V. bag deflates. The unit will operate at all patient attitudes, i.e., prone, sitting or standing, or in unusual environments, such as decompression chambers, high flying aircraft, iron lungs, in spacecraft or high pressure environments. The I.V. fluid is delivered at a pre-set constant rate of flow, despite a change of conditions. The system can operate at flow rates as low as 10 ml/hr and as high as hyper-alimentation rates.

The invention solves many of the above-noted problems and lends itself to be adapted to further feedback control by monitoring certain patient vital signs. The device can be adjusted to compensate for changes in blood pressure which normally have an adverse effect on standard intravenous delivery systems. For example, the unit can provide high pressure flow to overcome occurrences such as collapsed veins. Furthermore, the unit is virtually noiseless as the low power stepper motor drives the throttle valve only occasionally when a change in valve setting is required to maintain the programmed flow rate.

BRIEF DESCRIPTION OF THE DRAWING

Preferred embodiments of the invention will be described hereinbelow with reference to the drawings wherein:

FIG. 1 is a view of the ambulatory intravenous delivery system of the invention;

FIG. 2 is a cross-sectional view of the container taken along lines 2—2 of FIG. 1;

DESCRIPTION OF THE PREFERRED EMBODIMENT

Figure 3:
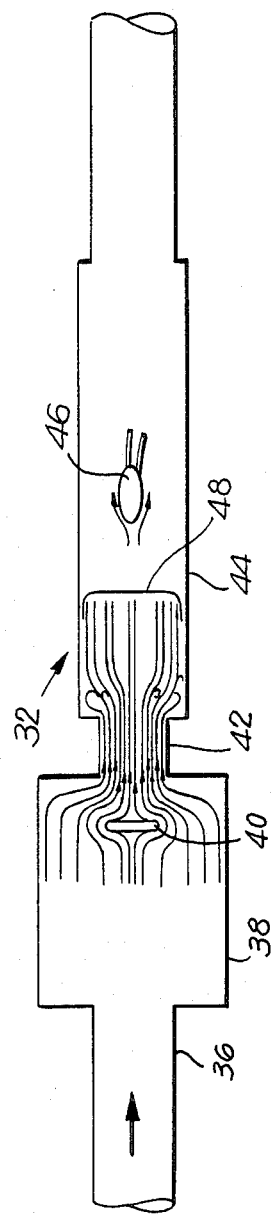
FIG. 3 is a schematic view of the flow meter of the present invention.

The I.V. fluid delivery system includes four major components, a pressurized source of fluid, a flow meter, a throttle valve and control means to adjust the throttle valve according to readings from the flow meter.

Referring initially to FIGS. 1 and 2, the pressurized source of fluid includes an I.V. bag 10 of the type having two compartments, 11 and 11A. The first compartment 11 is filled with the fluid to be dispensed and is separated from a second compartment 11A by membrane 13. Such fluids which are contemplated include hyperalimentation fluids, liquids such as saline solutions, nutritional solutions, chemotherapeutic solutions, drugs which may be administered intravenously, or the like. The second compartment communicates with a source of pressure, preferably a gas under pressure. In the preferred embodiment the source of pressurized gas is a COhd 2 cartridge 12 contained in a common piercing-type activating apparatus 14. When the $CO_2$ cartridge is placed within the piercing apparatus and cap 16 is threaded onto base 18, a hollow needle pierces cartridge 12 and allows the $CO_2$ gas contained under pressure to escape through tube 20.

Tube 20 communicates with a regulator valve 22. Pressure gauge 24 is mounted on the low pressure side (I.V. bag side) of the regulator valve 22. The low pressure side of regulator valve 22 communicates with the second compartment 11A of I.V. bag 10.

In operation the $CO_2$ cartridge 12 serves as a high pressure gas supply, and regulator valve 22 is adjusted by either physician or patient to obtain the desired pressure. The pressure may be checked through gauge 24. Through this apparatus a constant pressure is maintained in the second compartment of the I.V. bag. The second compartment exerts pressure on the first compartment and squeezes the I.V. fluid out of the first compartment under pressure through tube 26.

Figure 6:
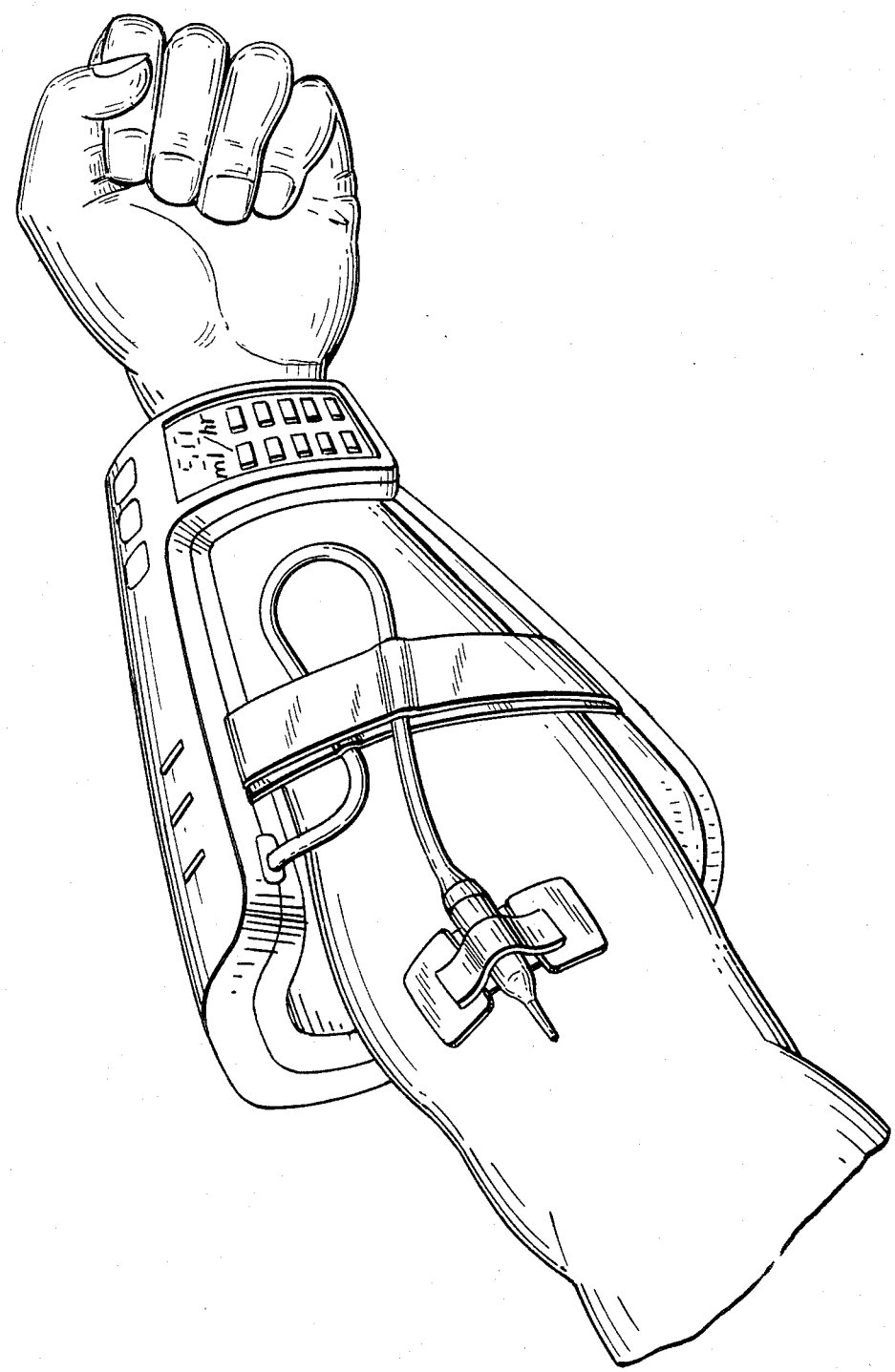
FIG. 6 is a perspective view of a human forearm mounted embodiment of the invention.
Figure 7:
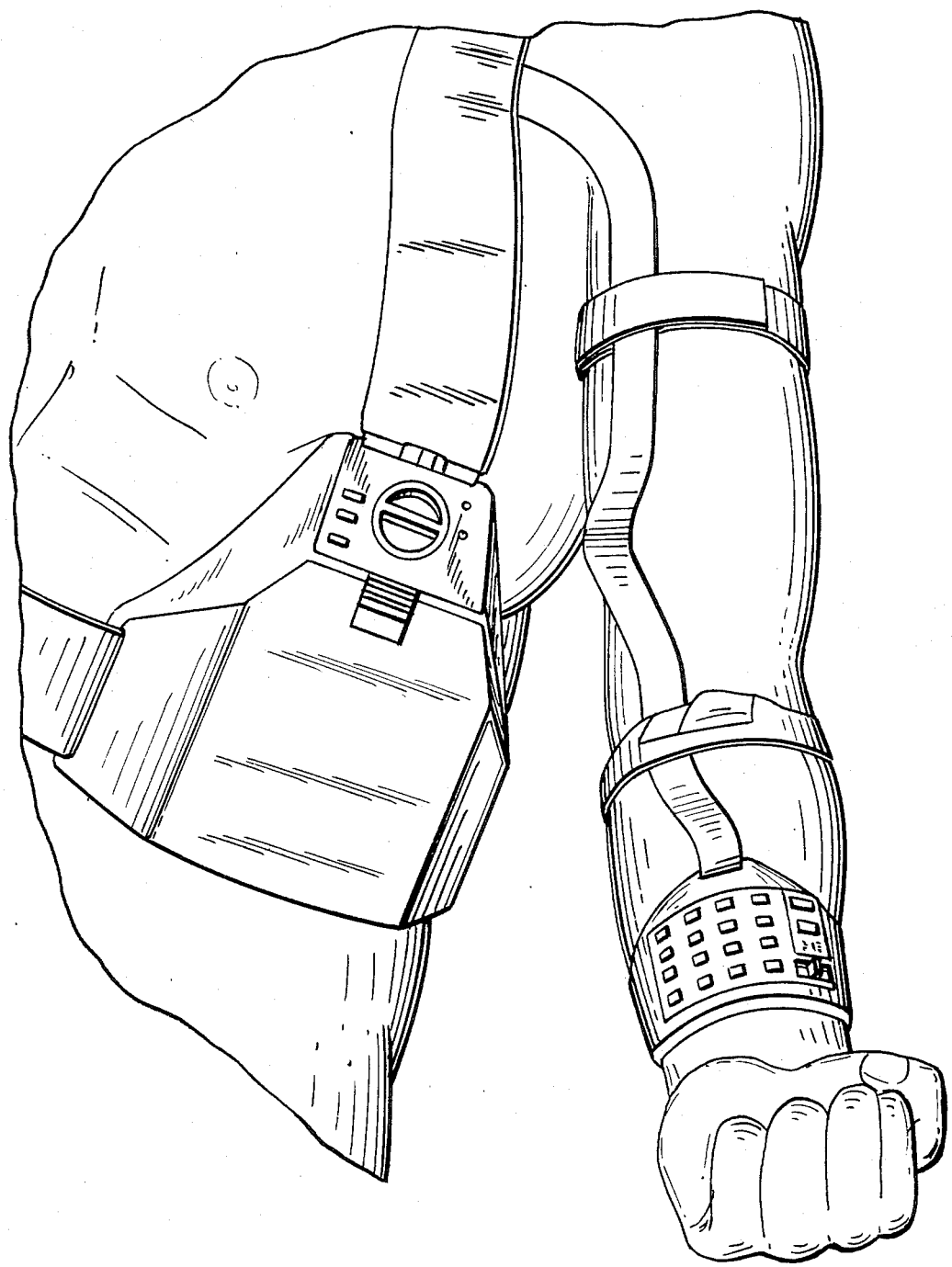
FIG. 7 is a perspective view of a belt mounted embodiment of the invention.

Tube 26 is provided with a valve or shut-off 28. Shut-off 28 allows the patient or doctor to manually stop the flow through tube 26. Thus, in operation, I.V. fluid is supplied, under pressure, through tube 26 regardless of the position or orientation of the bag 10. Although the bag 10 is shown vest mounted in FIG. 1, because of the pressurizing apparatus the bag may be located on the patient's forearm as shown in FIG. 6 or a hip belt as shown in FIG. 7.

The system has a metering and control apparatus 30, which serves two separate functions. Flow meter 32 shown in FIG. 3 monitors the flow rate of the I.V. solution and control valve 34 shown in FIG. 4 controls the flow rate of the liquid.

Referring to FIG. 3, the flow meter comprises a tubular portion 36, an expanded section 38, which encloses chip resistor 40, a step constriction 42 and widened section 44 which encloses a thermistor 46. The relative cross-sectional areas are illustrated in FIG. 3.

In operation the I.V. fluid flows through expanded section 38 in a substantially laminar flow condition. An electrical current is directed through chip resistor 40 which becomes heated and in turn heats the fluid which wipes it as it flows by. The heated fluid then flows through step constriction 42 which increases the fluid velocity through the well-known venturi effect. The fluid moves into widened portion 44 with an attendant turbulence as illustrated caused by the step expansion which causes the fluid to form a substantially planar heat wave front 48 to be formed in the fluid as shown. The mixing which occurs in the fluid while passing through step constriction 42 and widened portion 44 assures even distribution of the heated portion. When wave front 48 passes thermistor 46, which is of 100K ohm resistance such as the B07 or B09 series manufactured by Thermometrics (or similar thermistor), the temperature rise is detected. Electronic means described below are provided to compare the flow rate determined by the time it takes the heated slug of fluid to travel from chip resistor 40 to thermistor 46 and the "command" flow rate preset by the operator.

This novel flow meter can measure flow rates as low as 10 ml/hr. Without the unique cross-sectional shape the laminar flow within the tube would allow the central portion of the fluid element to reach the thermistor faster than elements along the edge of the tube giving spurious readings. Cooling of the fluid as it passes the heater can also cause errors if there isn't enough temperature rise of the faster moving fluid to trigger the thermistor sensory circuit.

As in some common circuits, we do not measure time per se, but combine the elapsed time it takes for the heat pulse to be sensed at the thermistor implicitly with an adjustable oscillator frequency to obtain correction pulses for direct activation of control valve 34 by suitable means such as stepper motor 50 shown in FIG. 1. This provides linearity without precalculated calibration corrections. The pulse comes directly from a battery 51.

The thermistor is in a capacitively coupled bridge circuit on the input of an operational amplifier. The coupling prevents slowly changing resistance variations of the thermistor from registering as a sensed signal. In this way only a rapidly occurring drop in resistance will cause the amplifier to issue a pulse. The sensed pulse is displayed.

Figure 4:
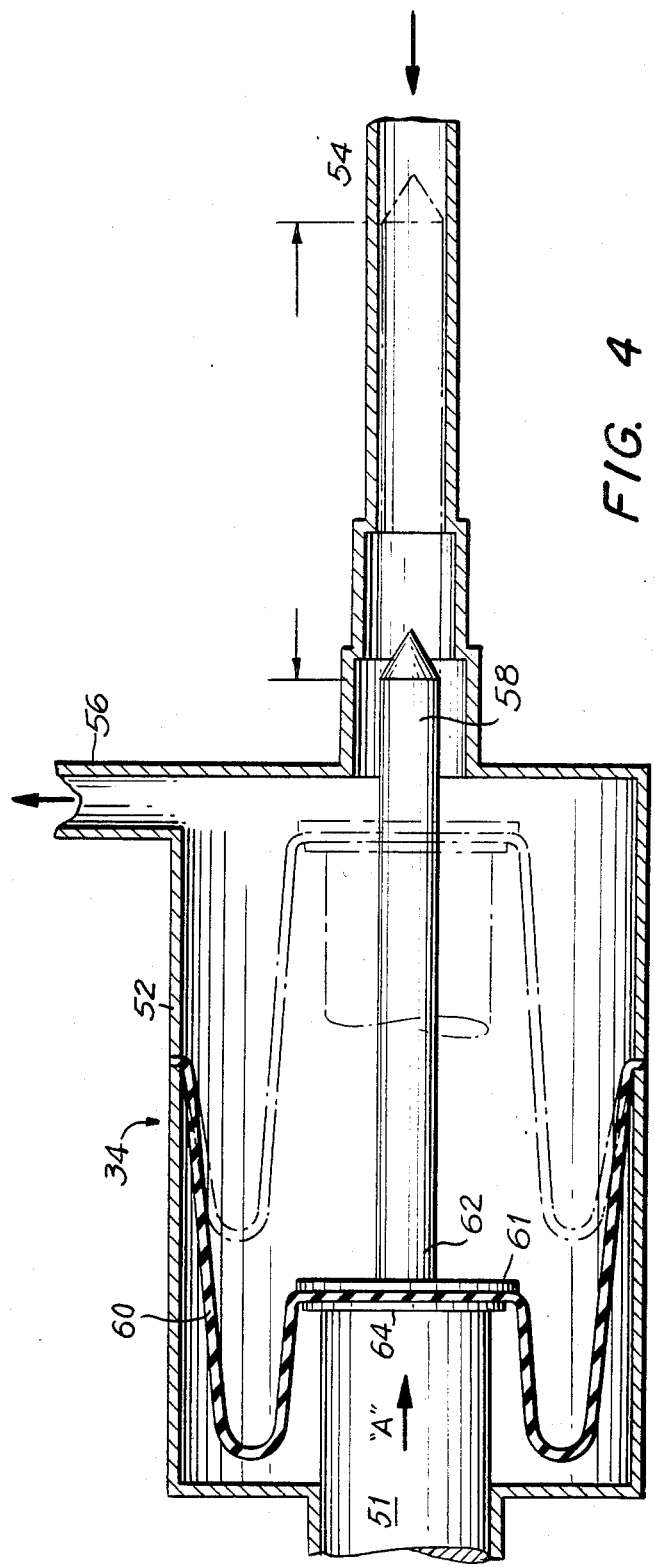
FIG. 4 is a cross-sectional view of the fluid control throttle valve of the invention.

Adjustments to the flow rate are made by a control valve such as the throttle valve 34 shown in FIG. 4. The throttle valve 34 is operated by stepper motor 50 shown in FIG. 1. The stepper motor's coils are energized by four transistors, where the activation sequence is controlled by the count output of an up/down counter. When activated, the stepper motor 50 moves shaft 51 in the axial direction by discrete amounts.

Referring once again to FIG. 4, the throttle valve 34 comprises housing 52 with an inlet tube 54 and an outlet tube 56. Pin 58 is disposed within the housing and moves partially within inlet tube 54. A flexible diaphragm 60 is provided to seal the inside of the valve from the introduction of air.

The fluid flow rate is controlled by the distance which pin 58 extends into inlet tube 54, and the gap between pin 58 and inlet tube 54, according to the equation:

$$Q = \left(\frac{\pi \Delta P}{6\mu L}\right) (r) (g)^3 (1.02 \times 10^8)$$

where
Q = flow rate (ml/hr)
$\Delta P$ = pressure drop across the needle valve (psi)
r = radius of the pin (inches)
g = gap between the pin wall and the inlet tube wall (inches)
$\mu$ = viscosity of the fluid (lb-sec per FT$^2$)
L = length which the pin extends into the inlet tube (inches)

Thus, it is seen that by varying the distance (L) which the pin 58 extends into inlet tube 54, the flow rate (Q) may be adjusted.

Referring once again to FIG. 4, one end 62 of pin 58 is attached to flexible diaphragm 60 such that the diaphragm 60 flexes with the movement of pin 58. One end 64 of stepper motor shaft 51 is attached to the surface of diaphragm 60 opposite the surface to which pin 58 is attached. When the stepper motor 50 is energized, it causes shaft 51 to move in the axial direction as shown by arrow "A" in FIG. 4. If a slower flow rate is necessary, the shaft 51 will move inwardly of housing 52 causing the diaphragm 60 to flex and pin 58 to move further into inlet tube 54. This increases the frictional losses of the fluid flowing through the annular gap formed between pin 58 and tube 54 thus reducing the flow rate. To increase the flow rate, shaft 51 is withdrawn slightly thus decreasing the amount pin 58 extends into tube 54 and thereby increasing the flow rate of the fluid.

Because Q is a function of (1/L) and therefore the relationship is inherently non-linear, the inlet tube—and thus the orifice length—is stepped down as shown in FIG. 4 in order to compensate for non-linear effects. The control of the throttle valve allows a range from a maximum flow rate position to a fully closed position where collar 61 acts as a gasket to halt all flow, with relatively minor changes in the servo-loop gain.

Figure 8:
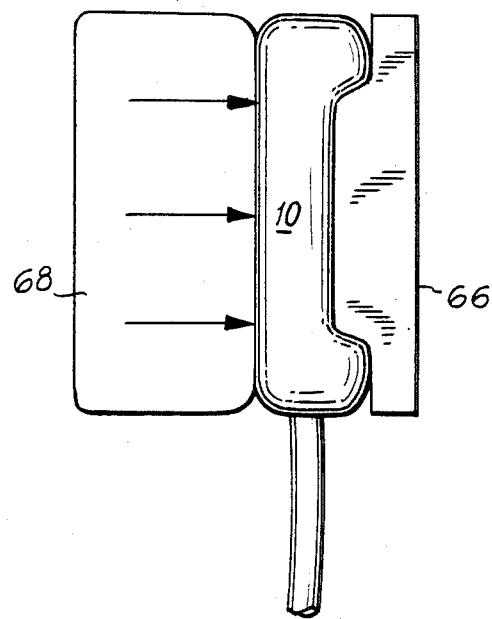
FIG. 8 is a top view of the I.V. bag of the invention, illustrating an alternate embodiment of a pressure source.
Figure 9:
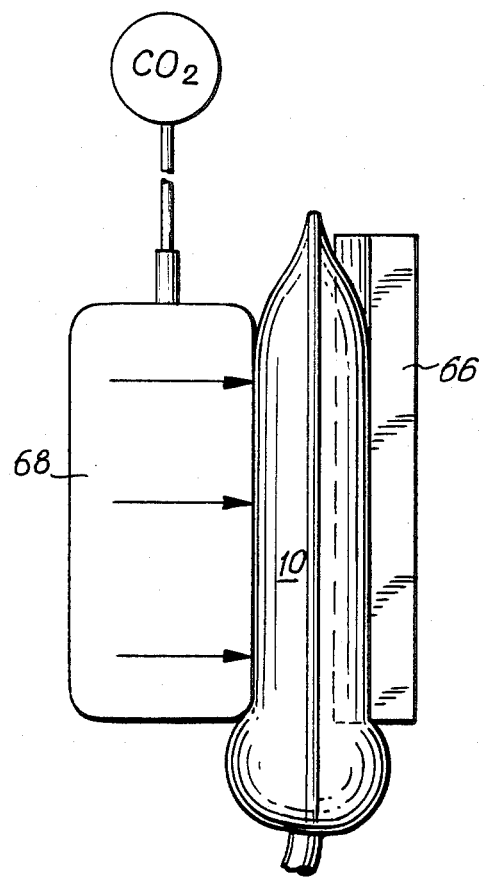
FIG. 9 is a side view of the I.V. bag of FIG. 8.

It should be understood that alternative pressure sources may be utilized to force the substance toward the recipient for delivery. One example is illustrated in FIGS. 8 and 9. In this alternative, the I.V. bag 10 has positioned on one side a fixed support 66 and a pressurized bladder 68 on the other side. As shown in one side view of FIG. 9, a suitable source of pressure for the bladder 68 may include a $CO_2$ pressure source as described hereinabove, or alternately, an equivalent gas (or liquid) under pressure. As illustrated in the top view of FIG. 8, the fixed support 66 has an irregular configuration on the pressure side to permit a continuous volume of fluid in bag 10 to be maintained in communication with the fluid outlet thereby preventing fluid from becoming trapped in "pockets" which may develop in the bag. Still another alternative pressure source includes hand pump 21 illustrated schematically in FIG. 1. Hand pump 21 communicates with pressure line 20 via hand operable valve 23. These or equivalent pressure sources may be used as an alternative prime source of pressure, or as an auxiliary source of pressure in the event of a failure of the main pressure source.

Control Electronics

Figure 5:
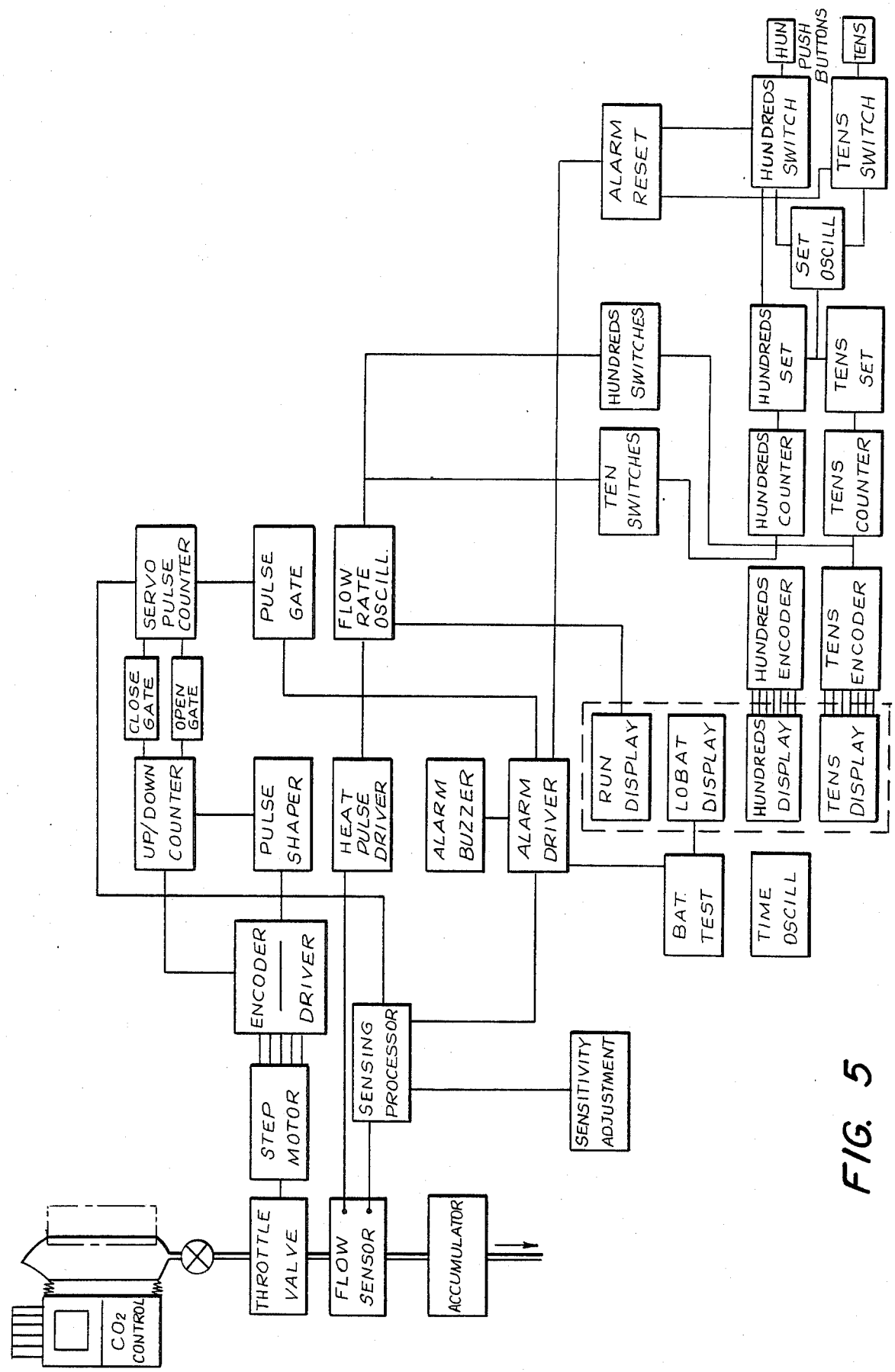
FIG. 5 is a block diagram of the control system of the invention.
Figure 10:
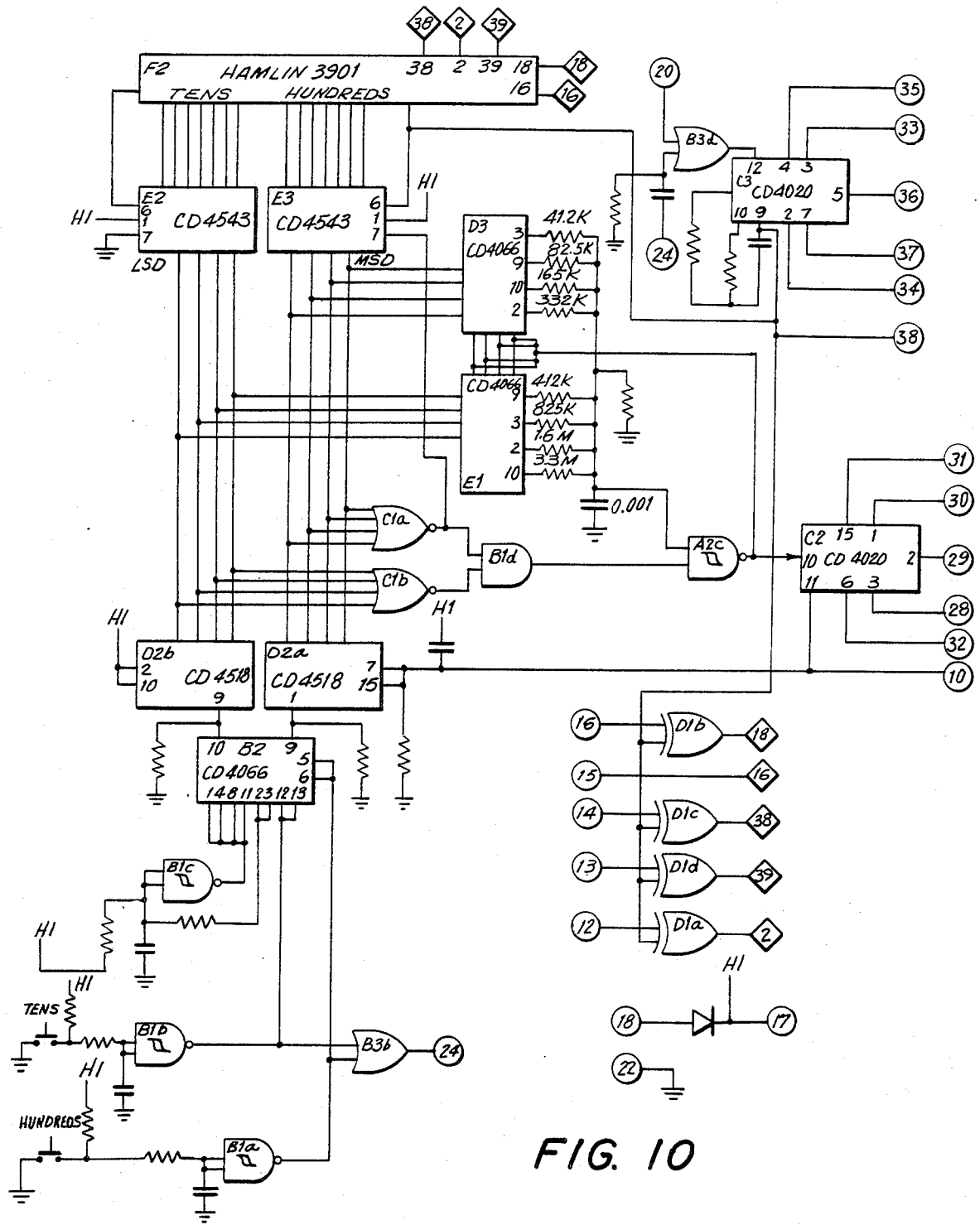
FIG. 10 is a schematic diagram of the display circuitry of the invention.
Figure 11:
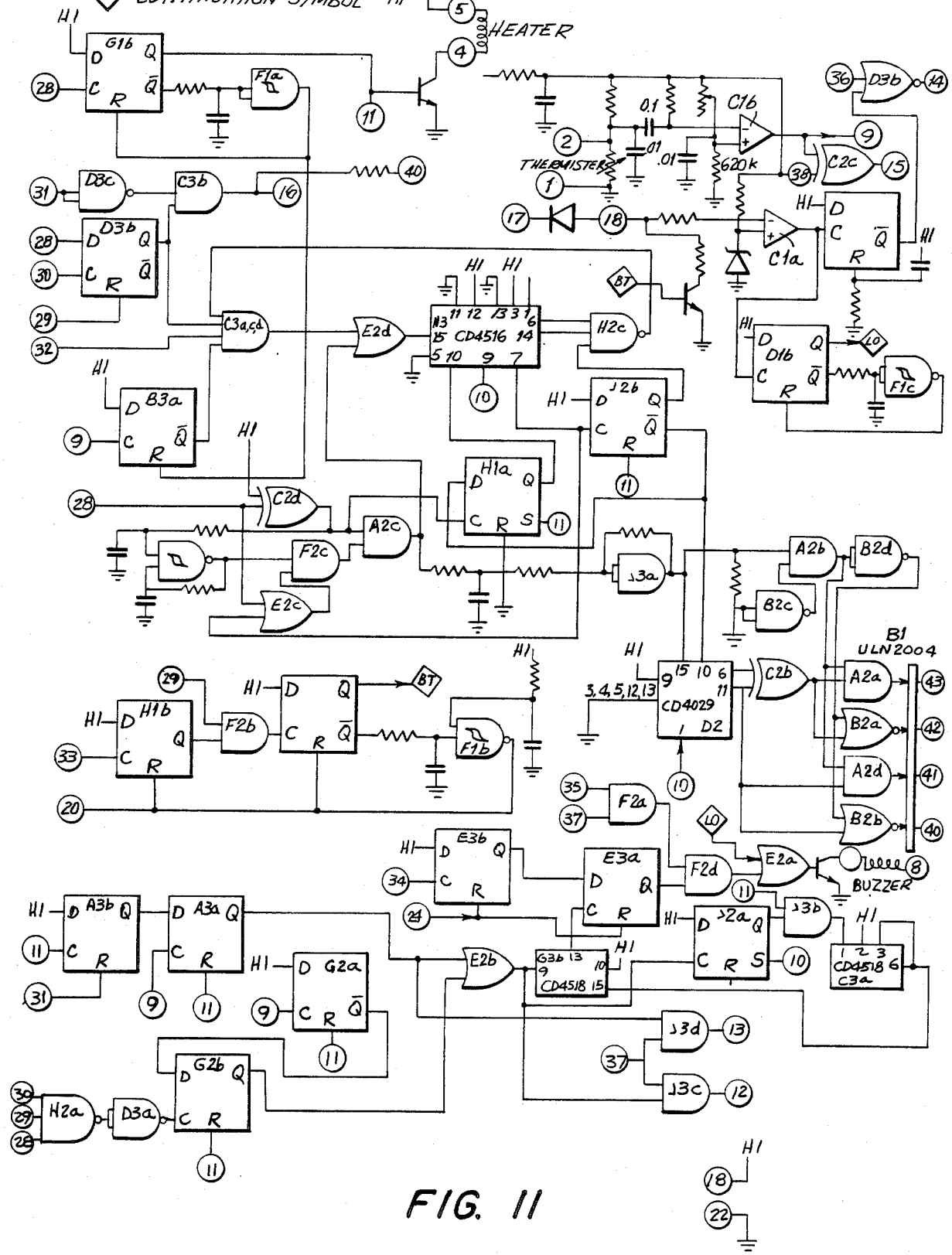
FIG. 11 is a schematic diagram of the control circuitry of the invention.

FIGS. 10 and 11 illustrate an exemplary electronic circuit described hereinbelow which can be used with the invention. FIG. 5 is a block diagram of the circuitry. However, it should be understood that alternate circuits, including programmable micro-processors, could be used to monitor vital functions and control the fluid flow. The electronic circuitry is used for a variety of functions including flow rate determination, flow control adjustment, display and low battery tests.

1. Major Circuit Subdivisions.

The control electronics consists of two circuit boards - Display and Control. The Display board has a liquid crystal display (LCD) which provides visual indication of the command flow rate requested by the operator, as well as certain "status" indications (i.e. low battery, overflow, underflow, requested rate and actual rate). This board also has two push buttons, one for setting the requested flow rate, "units" and one for setting the requested flow rates, "tens". "Units" and "tens" are used when flow is measured in drops per minute; however, "hundreds" and "tens" are used when flow rate is measured in milliliters per hour. Depressing either button silences the alarm buzzer for about 2½ minutes in addition to setting the rate. The control electronics, alarm buzzer, sensitivity adjustment and 5-pin DIN interface sockets are mounted on the control board. One of the sockets provides the connection to the flow valve control motor and the other to the flow rate sensor.

A small 9-volt battery plugs into a connector which is wired to the card-edge connectors that support the two circuit boards. The card edge connections are listed in Table I which follows.

TABLE I

| Card Edge Connections | | | |
|---|---|---|---|
| DISPLAY | | CONTROL | |
| 1 | | 1 | Therm. Gnd. |
| 2 | | 2 | Therm. Hi(I) |
| 3 | | 3 | |
| 4 | | 4 | Heater Lo(0) |
| 5 | | 5 | Heater Hi(0) |
| 6 | | 6 | |
| 7 | | 7 | Buzz Lo(0) |
| 8 | | 8 | Buzz Hi(0) |
| 9 | | 9 | Sense(0) |
| 10 | I(0) | 10 | I(I) |
| 11 | | 11 | Heat Pulse(0) |
| 12 | -Disp(I) | 12 | -Disp(0) |
| 13 | Disp(I) | 13 | Disp(0) |
| 14 | Lo Bat Disp(I) | 14 | Lo Bat Disp(0) |
| 15 | Sense Disp(I) | 15 | Sense Disp(0) |
| 16 | Cmd Disp(I) | 16 | Cmd Disp(0) |
| 17 | HI(0) | 17 | HI(0) |
| 18 | HI(I) | 18 | HI(I) |
| 19 | | 19 | |
| 20 | Timer Reset(I) | 20 | Timer Reset(0) |
| 21 | | 21 | |
| 22 | Gnd | 22 | Gnd |
| 23 | | 23 | |
| 24 | Alarm Reset (0) | 24 | Alarm Reset(I) |
| 25 | | 25 | |
| 26 | | 26 | |
| 27 | | 27 | |
| 28 | Q14(0) | 28 | Q14(I) |
| 29 | Q13(0) | 29 | Q13(I) |
| 30 | Q12(0) | 30 | Q12(I) |
| 31 | Q11(0) | 31 | Q11(I) |
| 32 | Q7(0) | 32 | Q7(I) |

TABLE I-continued

| Card Edge Connections | | | |
|---|---|---|---|
| DISPLAY | | CONTROL | |
| 33 | TQ14(0) | 33 | TQ14(I) |
| 34 | TQ13(0) | 34 | TQ13(I) |
| 35 | TQ6(0) | 35 | TQ6(I) |
| 36 | TQ5(0) | 36 | TQ5(I) |
| 37 | TQ4(0) | 37 | TQ4(I) |
| 38 | TQ0(0) | 38 | TQ0(I) |
| 39 | | 39 | Motor Hi(0) |
| 40 | | 40 | |
| 41 | | 41 | |
| 42 | | 42 | Motor (0) |
| 43 | | 43 | |
| 44 | | 44 | |

2. Display Functions

The circuit diagram of the display board is shown in FIG. 10. In addition to the LCD mounted in location F2, there are display drivers (E2 for the units and E3 for the tens), and the counter. in location D2 whose output are the two binary-coded decimal digits set by operating the push buttons. When either button is depressed, an alarm reset signal is sent to the control board via connector pin 24, and a digit advance oscillator is activated, feeding clock pulses to the appropriate BCD section of the counter at the D2 location. These counters sections are initially set to zero by a pulse on the initiating line (connector pin 10) as soon as the battery is plugged into the unit.

A null detection circuit consisting of gates B1D and C1 serves to block the cycling of the flow rate oscillator A2C if the requested rate is zero, and also blanks out the zeros in the LCD. The BCD signals generated by the D2 counter control solid state switches in locations D3 and E1, which modify the feed-back resistance of the flow rate oscillator A2C so that the oscillation frequency is proportional to the requested rate setting displayed. A binary counter in location C2 generates a number of subdivisions of the flow rate oscillator frequency ($Q_7$ and $Q_{11}$ to $Q_{14}$) appearing on Pins 28–32 of the card edge connector.

A time reference oscillator and counter is located at C3. The basic reference frequency required for the LCD operation is approximately 32 hz, which is also used by the XOR gates in location D1 for the status displays generated by the control board and introduced on pins 12–16 of the connector. The various time signals generated by the time reference oscillator are made available on pins 33–38 of the connector. The time reference oscillator is set to zero either by depressing one of the display-setting push buttons or by a 5-minute reset signal coming from the control board on pin 20.

Connector pin 18 is the positive voltage battery input. Ground connection 22 goes to the negative battery terminal.

3. Control Functions

The control functions shown in the diagram of FIG. 11 are divided into the following major subgroups:
A. Flowmeter
B. Flow Interval Detector
C. Valve Drive Generator
D Alarm Functions.
A. Flowmeter
(a) Heater.

The flowmeter requires short current pulses to be delivered to the chip resistor at regular intervals. Flip-flop G1B clocked by the $Q_{14}$ signal of the flow rate oscillator and reset by gate F1a drives one of the output transistors at B1 to ground connector pin 4, which is connected to one of the heater resistance leads. The heat pulse drive signal on pin 13 of flip-flop G1B is used as a reference pulse in several other circuits on the board. It is also brought out on connector pin 11 for monitoring purposes. The heater leads are on pins 4 and 5.

(b) Sensor

A thermistor of approximately 100K ohm resistance located downstream from the heater and connected to pins 1 and 2 picks up the heat pulse carried by the fluid. The thermistor is in a capacitively coupled bridge circuit on the input of operational amplifier C1b. The coupling prevents slowly changing resistance variations of the thermistor from registering as a sensed signal. Only a rapidly occurring drop in resistance will cause the amplifier to issue a pulse. A manually adjustable potentiometer is used to set the threshold level of the sensing ciruit.

The sensed pulse is displayed as the decimal point after the units LCD digit. This decimal point display is the actual drop incidence signal sensed by the flowmeter. The pulse signal is also brought out on connector pin 9 for monitoring purposes.

B. Flow Interval Detector.

A presettable 4-stage binary up-down counter located at H3 monitors the timing of the flowmeter output pulses in relation to the requested rate pulses. The binary counter is preset to the count of 10 (equivalent to $-6$) by the heat pulse signal. The clocking signal to the counter comes from either of two sources via gate E2d; flow rate oscillator (from connector pin 32) or motor pulse oscillator F1d. The latter is a part of the valve drive generator and will be discussed below in section C.

The flow rate oscillator pulses occurring at 128 times the heat-pulse frequency (i.e., the $Q_7$ rate) are gated to the counter through gate C3, which prevents the clocking of the counter under any of the following three conditions:

(1) fewer than 16 $Q_7$ pulses have passed following the heat pulse (governed by flip-flop B3b);

(2) a sense pulse has occurred (governed by flip-flop B3a); and (3) the counter has reached the count of 5 (governed by gate H2c).

Following the heat pulse, which sets flip-flop H1a, the counter is initially in the "count up" state. It is thus evident that with the 16th $Q_7$ pulse the counter advances from $-6$ upward, stopping either when a sense pulse arrives or when it reaches the count of 5. In terms of $Q_7$ pulses, the counter registers counts as shown in Table II below.

TABLE II

| $Q_7$ Pulses After Heat Pulse | H3 Counter States Count On H3 |
| --- | --- |
| 1 | 10 |
| 2 | 10 |
| 3 | 10 |
| : | : |
| 14 | 10 |
| 15 | 10 |
| 16 | 11 |
| 17 | 12 |
| 18 | 13 |
| 19 | 14 |
| 20 | 15 |

TABLE II-continued

| $Q_7$ Pulses After Heat Pulse | H3 Counter States Count On H3 |
| --- | --- |
| 21 | 0 |
| 22 | 1 |
| 23 | 2 |
| 24 | 3 |
| 25 | 4 |
| 26 | 5 |
| 27 | 5 |
| 28 | 5 |
| : | : |

Since a flowmeter sense pulse stops the counter via flip-flop B3a and gate C3, the counter output after the sense pulse can be used to determine the timing of the sense pulse. If the counter reads 10, the sense pulse occurred before the 16th $Q_7$ pulse. If the counter reads 5, the sense pulse occurred after the 26th $Q_7$ pulse. Counter states between these extremes represent the corresponding timing of the sensor pulse. Gates C3b and D3c are used to display, via pin 16, the time period spanned by the 16th to 24th $Q_7$ pulses as a bar next to the actual sense-pulse decimal point display. The bar display shows the interval during which the sense pulse is normally received. Its frequency is proportional to the requested flow rate. This display is useful in judging whether the system is functioning properly, i.e., whether the actual sense pulse (decimal point) occurs within the requested incidence range (bar) and whether the system responds correctly to forced deviations.

C. Valve Drive Generator.

The flow control valve is driven by a stepper motor whose coils are energized by four output transistors in DIP B1. The sequence of transitor activation is controlled by the count output of an up/down counter located at D2. When that counter receives a clocking pulse on its pin 15, gates A2, B2, and C2 cause motor pulses to occur in such a way that the angular position of the stepper motor shaft follows the count output - increasing count pulses corresponding to valve closing motion and decreasing count pulses to valve opening motion.

Following the heat pulse, counter D2 is in the up-count state as governed by flip-flop J2b. If and when the H3 counter is stepped from 0 to 1, the motor drive counter D2 is transferred to the down-count state by J2b. Flip-flop J2b also causes gate C3a to remain open via gate H2c until the H3 counter has stepped past zero before enabling the stopping action at count 5 (when $Q_1$ and $Q_3$ are both High again).

The clock pulses which eventually drive the valve motor originate at oscillator F1d. This oscillator is locked in the High state for 63 $Q_7$ pulses after the heat pulse has occurred. On the 64th $Q_7$ pulse the oscillator begins to send pulses through gates A2c and F2c to both counters H3 and D2. With $Q_{14}$ Low during this time, gate E2c permits only enough pulses to pass until counter H3 reaches 0, counting up if the sense pulse occurred early or down if it occurred late. The up-down control is provided by flip-flop H1a, which is set to the same up/down state as counter D2 at the moment when the $Q_{14}$ signal goes Low. The last pulse in this return-to-zero count is so short that it will not pass the delay circuit around gate J3a, thereby preventing counter D2 from running ahead of the slowly moving stepper motor.

To illustrate the operation of the control system, assume for example that counter H3 stopped at count 12 because a sense pulse came in right after the 17th $Q_7$ pulse. J2b had not been clocked yet because counter H3 did not pass zero. Hence both D2 and H3 counters remain in the up-count state. When $Q_{14}$ goes Low (after 63 $Q_7$ pulses) the motor pulse oscillator pulses advance counter H3 and cause the motor to open the valve two steps (the count going from 12 to 13 and 13 to 14). As the H3 count goes from 14 to 15, the carry-out line H3-7 goes Low, which cuts the pulse short via gate E2c so that it neither advances D2 nor steps the motor.

As another example, assume that H3 stopped at count 3 because a sense pulse arrived right after the 24th $Q_7$ pulse. J2b was clocked two pulses earlier when H3 passed 0. Hence D2 is now in the down-count state and the D line H1-5 of H1a will cause counter H3 to switch to the down-count state also when $Q_{14}$ goes Low some 40 $Q_7$ pulses later. The motor pulse oscillator signals which commence after the 64th $Q_7$ pulse then decrement counter H3 and cause the motor to close the valve two steps (the count going from 3 to 2 and 2 to 1). As the H3 count goes from 1 to 0, the carry-out line H3-7 goes Low, which cuts the pulse short via gate E2c so that it neither decrements D2 nor steps the motor.

As a third example, assume that the sense pulse occurred immediately after the counter had entered state 15. The carry-out line is Low and C3d blocks any further pulses from reaching the counter. The counter simply remains in state 15 until the next heat pulse presets it to 10. No pulses are passed to the motor control gates A2 and B2.

If the sense pulse occurred right after the counter had entered state 1, the counter would stop there and the carry-out line would go Low as soon as the count direction control is switched from up to down on the 64th $Q_7$ pulse by flip-flop H1a. With the carry-out line Low, gate E2c would prevent any pulses from reaching the motor.

D. Alarm Functions.

(a) Low Battery.

Every five minutes the time reference oscillator generates a signal which places a 30 ohm load on the battery for 5 microseconds via flip-flops G1a and H1b and gates F1b and F2b. These gates are used to confine the battery test to an interval when no other controlling functions are active. The battery voltage is monitored continuously by amplifier C1a, which compares the battery with a zener diode reference voltage. When the battery voltage under load falls below the reference level, the alarm buzzer is turned on for about ¼ second and the LO BAT display flashes as controlled by flip-flop D1a and gate D3b. The display stops flashing only when the battery is disconnected, but the buzzer beeps just once every time the battery voltage drops below its reference from a higher level.

(b) Overflow/Underflow.

Flip-flops A3 and G2 monitor the timing of the sense pulse with respect to the 8th and 48th $Q_7$ pulses. Considering that the system responds with varying degrees of flow valve adjustments over the range of the 15th to 26th pulses as seen in Table II, the occurrence of a sense pulse before the 8th $Q_7$ pulse is interpreted as a gross overflow condition, and occurrence of the sense pulse after the 48th $Q_7$ pulse as a gross underflow condition.

As these conditions occur, the display flashes either plus (i.e. +) or minus (i.e. −) via gates E2b and J3c,d.

Every time either of these conditions are sensed, counter G3b is clocked. When this counter reaches the count of 4, it activates the alarm buzzer via flip-flop E3a with a continuing rhythmic buzz signal, which can be turned off for 2½ minutes by briefly depressing either one of the control buttons. Counter G3b is reset upon the occurrence of the 8th heat pulse by counter G3a after the first abnormal flow condition is sensed. Hence there will be no alarm if fewer than 4 abnormal flow conditions occur during 8 consecutive heat pulses. Furthermore, the alarm buzzer is inhibited for 2½ minutes initially or after operation of either control button by flip-flop E3b.

The + and − display functions are not affected by the controls on the audible alarm described in the preceding paragraph.

We claim:

1. An apparatus for intravenous delivery of substances while permitting the recipient to be ambulatory comprising:
   (a) means for containing and delivering a substance to be delivered to the recipient, said containing means capable of being supported and carried by the recipient;
   (b) means for providing pressure to the substance to be delivered;
   (c) means to control the flow rate of the substance to the recipient;
   (d) meter means positioned within the flow path of said substance to determine the flow rate of the said substance, said meter means including heating means disposed to supply heat to a portion of said substance as it flows, detecting means disposed to detect temperature changes in the substance such that a pulse of heat may be intermittently added to said substance by said heating means and detected downstream by said detecting means to determine the flow rate of said substance; and
   (e) means to adjust said flow control means in response to said signal indicating the flow rate so as to maintain a predetermined flow rate of the substance.

2. The apparatus according to claim 1 wherein said containing means comprises a container having at least two compartments separated by means to transfer pressure therebetween, a first compartment for containing said substance and communicating with delivery means and a second compartment communicating with a source of pressurized gas such that pressure provided in said second compartment acts on said first compartment to provide pressure to force said substance out of said first compartment.

3. The apparatus according to claim 2 wherein the pressure within said second compartment is regulated by regulator means disposed between said source of compressed gas and said second compartment.

4. The apparatus according to claim 2 wherein said source of pressurized gas is a cartridge containing pressurized gas.

5. The apparatus according to claim 4 wherein said cartridge is a $CO_2$ cartridge.

6. The apparatus according to claim 1 wherein said flow control means comprises an exit tube, an inlet tube having a wall of predetermined diameter, a reservoir portion which communicates with said exit tube and said inlet tube, a control pin of predetermined diameter which is less than said first mentioned diameter and movably disposed within said inlet tube such that flow of a fluid through said inlet tube must flow through the annular gap between said pin and the wall of said inlet tube, and means to adjust the distance which said pin extends into said inlet tube.

7. The apparatus according to claim 6 wherein the diameter of said inlet tube increases in the direction of flow to increase the size of said annular gap.

8. The apparatus according to claim 1 wherein said meter means includes a first tubular section, a second tubular section of lesser cross-sectional area than said first section, a third section of cross-sectional area larger than said second section, said second section being disposed between said first and third sections, said heating means being disposed within said first section to supply heat to a portion of said substance as it flows therethrough, and said detecting means being disposed within said third section to detect temperature changes in the substance as it flows therethrough such that a pulse of heat may be intermittently added to the substance by said heating means and detected downstream by said detecting means to determine the flow rate of the substance.

9. The apparatus according to claim 8 wherein said heating means is a chip electrical resistor.

10. The apparatus according to claim 8 wherein said detecting means is a thermistor having resistance which varies with temperature.

11. The apparatus according to claim 1 wherein said means to determine the flow rate of the substance and signal producing means further comprises electronic circuitry.

12. The apparatus according to claim 1 wherein said means to adjust said flow control means comprise a stepper motor controlled by said electronic circuitry and connected to said flow control means.

13. An apparatus for regulating the flow rate of a fluid comprising a housing with an inlet opening to allow fluid to enter said housing and an outlet opening to allow fluid to exit said housing, said inlet opening being circular and communicating with an inlet tube of cylindrical internal wall shape having an internal diameter, a cylindrical pin of lesser diameter than said internal diameter with a first portion disposed for movement within said inlet tube and forming an annular gap between said internal wall and the cylindrical surface of said pin, said pin having a second portion which extends into said housing, means activated by a stepper motor to move said pin in discrete incremental amounts to adjust the distance which said pin extends into said inlet tube to thereby adjust the length of the annular gap through which said fluid flows.

14. The apparatus according to claim 13 wherein said means to move said pin comprises a flexible diaphragm disposed within said housing to separate and seal a first volume portion of said housing from a second volume portion, said inlet opening and said outlet opening communicating with said first volume portion, said second portion of said pin having an end, said end being fixed to a first surface of said diaphragm, a stepper motor with a shaft, said stepper motor capable of moving said shaft incremental amounts in the axial direction, said shaft having one end which movably extends into said housing to communicate with said second volume portion and fixed to said diaphragm on the reverse surface of said diaphragm such that when said stepper motor operates to axially move said shaft, said shaft flexes said diaphragm to move said pin.

15. The apparatus according to claim 13 wherein the internal diameter of said inlet tube progessively increases in the direction of fluid flow creating a progressively wider annular gap.

16. An apparatus for measuring fluid flow rate of a fluid comprising a conduit having a first section of predetermined cross-sectional area, a second conduit section having a step constriction of a lesser cross-sectional area, a third conduit section having a step enlargement of a greater cross-sectional area than said second section, said second section being disposed between said first section and said third section, heating means disposed within said first section to supply predetermined and pre-timed heat pulses to the substance, temperature detecting means disposed within said third section to detect temperature changes in the fluid as it flows through said third section, said fluid flowing first through said first section, then through said second section then through said third section and means to measure the time lapse between a heating pulse and the detection thereof by detecting means of the heated portion so as to determine the rate of flow of fluid through said sections.

17. The apparatus according to claim 16 wherein said heating means is an electrical resistor chip.

18. The apparatus according to claim 16 wherein said detecting means is a thermistor disposed within said third section of said meter means.

19. An apparatus for intravenous delivery of substances while permitting the recipient to be ambulatory comprising:
   (a) means for containing and delivering a substance to be delivered to the recipient, said means capable of being supported and carried by the recipient;
   (b) means for providing pressure to the substance to be delivered;
   (c) means to control the flow rate of the substance to the recipient;
   (d) chip resistor means positioned within the flow path of the substance to provide heat impulse to the substance;
   (e) heat sensing thermistor means positioned downstream of said chip resistor means to sense said heat impulse and to produce an electrical signal in accordance therewith; and
   (f) electronic means capable of receiving said thermistor signal and connected to said chip resistor means so as to process said signals to determine the time lapse between said heat impulse generated by said chip resistor means and the thermistor signal so as to determine the flow rate of the substance.

20. The apparatus according to claim 19 wherein said electronic means provides a signal to said flow control means to vary the flow rate of the substance in response to said flow rate determination and in comparison to a predetermined flow rate command.

21. The apparatus according to claim 20 wherein said means for providing pressure to the substance is a source of pressurized gas communicating with said container means.

22. The apparatus according to claim 21 wherein said source of gas is a source of $CO_2$ under pressure.

23. The apparatus according to claim 22 wherein said source of $CO_2$ under pressure is a $CO_2$ cartridge.

24. An apparatus for intravenous delivery of substances while permitting the recipient to be ambulatory comprising:
(a) means for containing and delivering a substance to be delivered to the recipient, said containing means capable of being supported and carried by the recipient;
(b) means for providing pressure to the substance to be delivered;
(c) means to control the flow rate of the substance to the recipient;
(d) meter means positioned within the flow path of the substance to determine the flow rate of the substance, said meter means including a first tubular section, a second tubular section of lesser cross-sectional area than said first section, a third section of cross-sectional area larger than said second section, said second section being disposed between said first and third sections, heating means disposed within said first section to supply heat to a portion of the substance as it flows therethrough, and detecting means disposed within said third section to detect temperature changes in the substance as it flows therethrough such that a pulse of heat may be intermittently added to the substance by said heating means and detected downstream by said detecting means to determine the flow rate of the substance; and
(e) means to adjust said flow control means in response to said signal indicating the flow rate so as to maintain a predetermined flow rate of the substance.

25. The apparatus according to claim 24 wherein said heating means is a chip electrical resistor.

26. The apparatus according to claim 24 wherein aaid detecting means is a thermistor having resistance which varies with temperature.

27. An apparatus for regulating the flow rate of a fluid comprising a housing with an inlet opening to allow fluid to enter said housing and an outlet opening to allow fluid to exit said housing, said inlet opening being circular and communicating with an inlet tube of cylindrical internal wall shape having an internal diameter, a cylindrical pin of lesser diameter than said internal diameter with a first portion disposed for movement within said inlet tube and forming an annular gap between said internal wall and the cylindrical surface of said pin, said pin having a second portion which extends into said housing, and means to move said pin which comprises a flexible diaphragm disposed within said housing to separate and seal a first volume portion of said housing from a second volume portion, said inlet opening and said outlet opening communicating with said first volume portion, said second portion of said pin having an end, said end being fixed to a first surface of said diaphragm, a stepper motor with a shaft, said stepper motor capable of moving said shaft incremental amounts in the axial direction, said shaft having one end which movably extends into said housing to communicate with said second volume portion and fixed to said diaphragm on the reverse surface of said diaphragm such that when said stepper motor operates to axially move said shaft, said shaft flexes said diaphragm to move said pin so as to adjust the distance which said pin extends into said inlet tube to adjust the length of the annular gap through which said fluid flows.

* * * * *